United States Patent [19]

Quinlan

[11] 4,188,359
[45] Feb. 12, 1980

[54] THIOETHER CONTAINING QUARTENARY AMMONIUM DERIVATIVES OF 1,4-THIAZINES

[75] Inventor: Patrick M. Quinlan, Webster Groves, Mo.

[73] Assignee: Petrolite Corporation, St. Louis, Mo.

[21] Appl. No.: 966,250

[22] Filed: Dec. 4, 1978

Related U.S. Application Data

[62] Division of Ser. No. 886,182, Mar. 13, 1978, Pat. No. 4,146,709.

[51] Int. Cl.$^2$ ............................................. C23F 11/04
[52] U.S. Cl. ............................... 422/12; 252/8.55 E; 252/391; 252/149; 422/16
[58] Field of Search ............. 252/391, 8.55 C, 8.55 E, 252/148, 149; 544/58, 59; 210/58, 59; 422/12; 424/246

[56] References Cited

U.S. PATENT DOCUMENTS

| 2,483,671 | 10/1949 | Risveschl | 544/59 X |
|---|---|---|---|
| 3,828,036 | 8/1974 | Quinlan | 544/58 |

OTHER PUBLICATIONS

Gilman et al., Chemical Abstracts, vol. 40, (1946), 84d.

Primary Examiner—Benjamin R. Padgett
Assistant Examiner—Josephine Lloyd Barr
Attorney, Agent, or Firm—Sidney B. Ring; Hyman F. Glass

[57] ABSTRACT

This invention relates to N-alkyl thioethers of quaternary ammonium derivatives of 1,4-thiazines; to the preparation thereof; and to the uses thereof for example as corrosion inhibitors, microbiocides, etc.

5 Claims, No Drawings

THIOETHER CONTAINING QUARTERNARY AMMONIUM DERIVATIVES OF 1,4-THIAZINES

This is a division of application Ser. No. 886,182, filed Mar. 13, 1978, now U.S. Pat. No. 4,146,709.

This invention relates to novel quaternary ammonium derivatives of 1,4-thiazines of the general formula

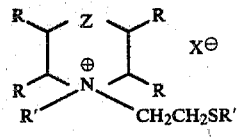

where R is hydrogen, a hydrocarbon group such as alkyl, etc., or a substituted hydrocarbon group. R' is a hydrocarbon group such as alkyl, cycloalkyl, aralkyl, etc. or a substituted hydrocarbon group. R'' is a hydrocarbon group such as alkyl, cycloalkyl, aralkyl, alkenyl, alkynyl, etc., or a substituted hydrocarbon group. Z is S, S→O, O←S→O, and X is an anion such as halide, sulfate, phosphate, nitrate, perchlorate or methyl sulfonate, ethyl sulfonate, vinyl sulfonate, etc. The preferred derivatives are those where R is hydrogen and it is further preferred that R' be an alkyl group having about 4 to 18 carbon atoms, a cyclohexyl group or a phenalkyl group and that R'' be an alkyl group having 1 to 8 carbon atoms, a cycloalkyl group, an alkynyl group, or an alkenyl group.

These compounds are prepared by reacting a divinyl sulfur compound with a thioether substituted secondary amine. The reaction of secondary amines with divinyl sulfur compounds is described in my U.S. Pat. No. 3,770,732 dated Nov. 6, 1973.

The reaction may be summarized by the following equation:

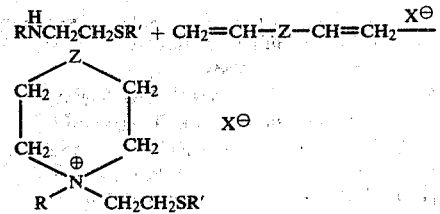

where R is alkyl, cycloalkyl, aralkyl, etc. and R' is alkyl, alkenyl, alkynl, aralkyl, cycloalkyl, etc. Z is S, S→O, O←S→O.

Examples of the divinyl sulfur compounds are:

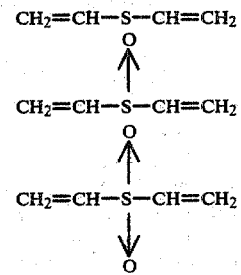

Examples of thioether substituted secondary amines capable of reacting with a divinyl sulfur compound to form the compounds of this invention include, for example:

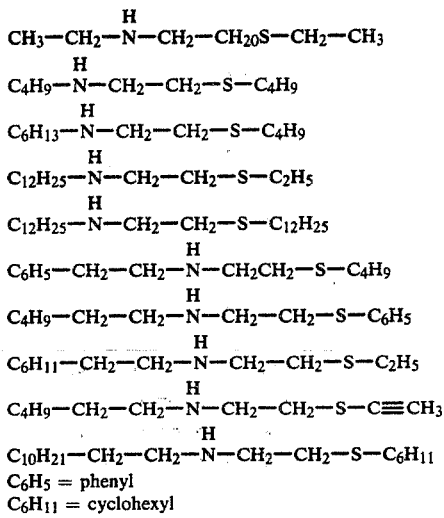

$C_6H_5$ = phenyl
$C_6H_{11}$ = cyclohexyl

These compounds are obtained in good yield by utilizing a modification of the procedure described by O. Landini and F. Rolla, Synthesis 1974, p. 565.

Suitable acids that may be employed to form the amine salts include hydrohalic acids such as hydrochloric, hydrobromic, hydroiodic, etc.; sulfuric, phosphoric, nitric, perchloric, methylsulfonic, ethylsulfonic, benzyl sulfonic, and the like.

In carrying out the reaction it is preferred to form the amine salt in situ, that is in a solvent such as ethanol in which it is soluble. However, if desired, the salt may first be isolated and purified. To the solution of the amine salt in a suitable inert solvent is added the divinyl sulfur compound. The preferred temperature is about 20° to 50° C. though higher or lower temperatures may be employed. A catalyst such as triethylamine may be used. In most instances the thiazine quaternary ammonium salt precipitates from the alcoholic medium and is purified by recrystallization. In some cases it is necessary to reduce the final volume in order to isolate the desired product.

The invention may be illustrated by the following examples.

EXAMPLE 1

Divinyl sulfone 5.9 g (0.05 mol) was added dropwise, with stirring, to a solution of

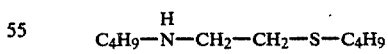

9.6 g. (0.05 mol) in 25 ml. of 4 N ethanolic hydrochloric acid. The mixture became warm and upon cooling crystals appeared. After 24 hrs. the crystalline product was filtered and washed several times with cold ethanol. The product was recrystallized from aqueous ethanol.

Yield: 14.6 g. (85%).

Anal. $C_{14}H_{30}ClNO_2S_2$—Calc. C, 48.91; H, 11.46; Cl, 10.32; S, 18.61; N, 4.07. Found: C, 48.89; H, 11.43; Cl, 10.29; S, 18.64; N, 4.11.

The product had the following structure which was confirmed by NMR spectrum.

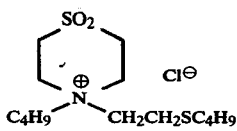

EXAMPLE 2

Divinyl sulfone 5.9 g. (0.05 mol) was added dropwise with stirring to a solution of

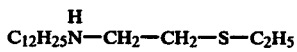

13.6 g. (0.05 mol) in 30 ml. of 4 N ethanolic hydrochloric acid. The resulting reaction mixture was heated at reflux for 2 hours. Upon cooling, a waxy solid separated. The solid was filtered and washed with cold ethanol.

Yield: 29 g (79%)

Anal.—Calc. N, 1.84; Found N, 1.75.

The product had the following structure

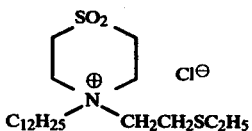

EXAMPLE 3

Divinyl sulfone 5.9 g. (0.05 mol) was slowly added to a solution of

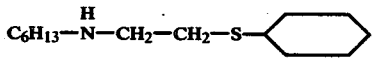

12.1 g. (0.05 mol) in 30 ml. of ethanol that had been acidified with 7.7 g. (0.06 mol) of hydroiodic acid. The reaction mixture becomes warm. After 24 hours the reaction mass contained a large mass of colorless crystals. The crystals were filtered and washed with cold ethanol.

Yield: 21 g. (90%).

The product was recrystallized from aqueous ethanol. It had the following structure:

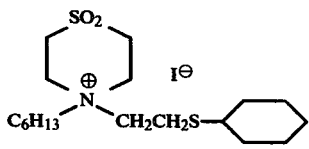

Anal.—Calcd. N, 2.98; S, 13.64; I, 27.08. Found N, 3.04; S, 13.48; I, 27.32.

In a similar manner the following examples were prepared.

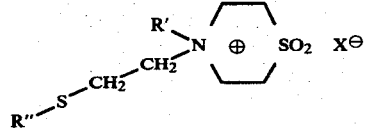

| Example | R' | R'' | X⁻ |
| --- | --- | --- | --- |
| 4 | $C_6H_5CH_2CH_2$ | $C_6H_5CH_2$ | Cl |
| 5 | $C_4H_9$ | $C_6H_{11}$ | Br |
| 6 | $C_{10}H_{21}$ | $C_2H_5$ | Br |
| 7 | $C_4H_9$ | $C_8H_{17}$ | I |
| 8 | $C_6H_{11}$ | $C_6H_{11}$ | I |
| 9 | $C_{14}H_{29}$ | $CH_3$ | $SO_3$ |
| 10 | $C_{18}H_{37}$ | $CH_3$ | I |
| 11 | $C_4H_9$ | $CH\equiv C-CH_2$ | Br |
| 12 | $C_4H_9$ | $C_6H_{13}-CH(CH_3)-$ | Cl |
| 13 | $C_{12}H_{25}$ | $CH_3$ | I |
| 14 | $C_4H_9$ | $CH_2=CH-CH_2$ | Br |

USES

This invention also relates to the inhibition of corrosion, particularly the corrosion of metals in contact with the acid solutions.

The present invention is especially useful in the acidizing or treating of earth formations and wells traversed by a bore hole. It may also be used in metal cleaning and pickling baths which generally comprise aqueous solutions of inorganic acids such as sulfuric acid, hydrochloric acid, phosphoric acid and are useful in the cleaning and treatment of iron, zinc, ferrous alloys, and the like.

If no corrosion inhibitor is present when the aqueous acidic solution comes in contact with the metal, excessive metal loss and consumption or loss of acid, and other adverse results will be experienced. There has been a continuing search for corrosion inhibitors which can be used effectively in small concentrations, and which are economical to produce. The need is also for corrosion inhibitors which are effective at high temperatures, e.g., 200° F. and above, such as are found in operations involving acidic solutions, particularly oil-well acidizing where higher and higher temperatures are found as the well extends further into the earth.

While the compounds of this invention are of themselves particularly good acid corrosion inhibitors, optionally they may be blended with acetylenic alcohols, dispersing and solubilizing agents such as ethoxylated phenols, alcohols, and fatty acids. They may also be blended with such known acid inhibitors as the quinoline or alkyl pyridine quaternary compounds or synergists such as terpene alcohols, formamide, formic acid, alkyl amine, alkylene polyamines, heterocyclic amines, and the like.

Quaternary ammonium compounds may be illustrated by C-alkyl pyridine-N-methyl chloride quaternary, C-alkyl pyridine-N-benzyl chloride quaternary, quinoline-N-benzyl chloride quaternary, isoquinoline-N-benzyl chloride quaternary, thioalkyl pyridine quaternaries, thioquinoline quaternaries, benzoquinoline quaternaries, thiobenzoquinoline quaternaries, imidazole quaternaries, pyrimidine quaternaries, carbazole quaternaries, the corresponding ammonium compounds, pyridines and quinolines may also be used alone or in combination with the quaternary compounds. Thus a pyridine plus quinoline quaternary, a quinoline plus quinoline quaternary, or quinoline or amine alone or in combination may be used.

The formic acid compound may be selected from the esters and amides of formic acid. The formic acid compound may be from the group consisting of formate esters of the structure:

HCOOR where R is a monoaryl group, an alkyl group having 1 to 6 carbon atoms, cyclo-alkyl residues having 5 to 6 carbon atoms, alkenyl and alkynl groups having 2 to 6 carbon atoms which may contain functional groupings selected from —C—OH, —OH, $=$C$=$O, —COOH, —SH, and NH$_2$. Examples of the formic acid compound are: methyl formate, ethylformate, benzyl formate, other alkyl and aryl formates, and the like. Other examples include formamide, dimethyl formamide, formanilide, and the like. Mixtures of the esters and mixtures of the amides may be used.

USE IN ACIDIZING EARTH FORMATIONS

The compositions of this invention can also be used as corrosion inhibitors in acidizing media employed in the treatment of deep wells to reverse the production of petroleum or gas therefrom and more particularly to an improved method of acidizing a calcareous or magnesium oil-bearing formation.

It is well known that production of petroleum or gas from a limestone, dolomite, or other calcareous-magnesian formation can be stimulated by introducing an acid into the producing well and forcing it into the oil or gas bearing formation. The treating acid, commonly a mineral acid such as HCl, is capable of forming water soluble salts upon contact with the formation and is effective to increase the permeability thereof and augment the flow of petroleum to the producing well.

Corrosion Test Procedure

In these tests the acid solutions were mixed by diluting concentrated hydrochloric acid with water to the desired concentrations.

Corrosion coupons of AISI 1020 Steel were pickled in an uninhibited 10% HCl solution for 10 minutes, neutralized in a 10% solution of NaHCO$_3$, dipped in acetone to remove water and allowed to dry. They were then weighed to the nearest milligram and stored in a desicator.

In most of the tests, a 25 cc/in$^2$ acid volume to coupon surface area ratio was used. After the desired amount of acid was poured into glass bottles, the inhibitor was added. The inhibited acid solution was then placed in a water bath which had been set at a predetermined temperature and allowed to preheat for 20 minutes. After which time, the coupons were placed in the preheated inhibited acid solutions. The coupons were left in the acid solutions for the specified test time, then removed, neutralized, recleaned, rinsed, dipped in acetone, allowed to dry, then reweighed.

The loss in weight in grams was multiplied times a calculated factor to convert the loss in weight to lbs./ft$^2$/24 hrs. The factor was calculated as follows:

$$\frac{\frac{144 \text{ in}^2}{\text{ft}^2}}{\frac{454 \text{ g}}{\text{lb}} \times \text{Surface Area of Coupon (in}^2) \times \frac{1 \text{ day}}{24 \text{ hrs.}}} = \text{Factor}$$

The results of these tests are included below:

| Inhibitor | p.p.m. | Test Temp °F. | Test Time Hrs. | Acid | Corrosion Rate (lbs./ft$^2$/day) |
|---|---|---|---|---|---|
| Ex. 1 | 2000 | 150 | 4 | 15% HCl | 0.075 |
| Ex. 2 | 2000 | 150 | 4 | 15% HCl | 0.029 |
| Ex. 3 | 2000 | 150 | 4 | 15% HCl | 0.050 |
| Ex. 6 | 2000 | 150 | 4 | 15% HCl | 0.041 |
| Ex. 9 | 2000 | 150 | 4 | 15% HCl | 0.031 |
| Ex. 10 | 2000 | 150 | 4 | 15% HCl | 0.030 |
| Ex. 11 | 2000 | 150 | 4 | 15% HCl | 0.035 |
| Ex. 13 | 2000 | 150 | 4 | 15% HCl | 0.025 |
| Ex. 14 | 2000 | 150 | 4 | 15% HCl | 0.068 |
| Blank | | 150 | 4 | 15% HCl | 0.275 |

Applications in which the inhibitors of the present invention are particularly useful include oil-well acidizing solutions, metal pickling, cleaning and polishing baths, boiler cleaning compositions and the like. They are also useful as oil soluble corrosion inhibitors, bactericides, water-in-oil demulsifying agents, surfactants and the like.

USE AS A MICROBIOCIDE

(I) In Water Treatment

This phase of the present invention relates to the treatment of water. More particularly, it is directed to providing improved means for controlling microbiological organisms including bacteria, fungi, algae, protozoa, and the like, present in water.

It is well known that ordinary water contains various bacteria, fungi, algae, protozoa and other microbiological organisms which, if uncontrolled, multiply under certain conditions so as to present many serious problems. For example, in swimming pools the growth of these microbiological organisms is very undesirable from a sanitary standpoint as well as for general appearances and maintenance. In industrial water systems such as cooling towers, condenser boxes, spray condensers, water tanks, basins, gravel water filters, and the like, microbiological organisms may interfere greatly with proper functioning of equipment and result in poor heat transfer, clogging of systems and rotting of wooden equipment, as well as many other costly and deleterious effects.

In other industrial applications where water is used in processes, as for example, as a carrying medium, etc., microbiological organisms may also constitute a problem in maintenance and operation. Illustrative of such industrial applications are the pulp and paper manufacturing processes, oil well flooding operations and the like.

The products of this invention are suitable as biocides for industrial, agricultural and horticultural, military, hygienic and recreational water supplies. They provide an inexpensive, easily prepared group of products which can be used, in minimal amounts, in water supplies, in cooling towers, air-conditioning systems, on the farm and ranch, in the factory, in civilian and military hospitals and dispensaries, in camps, for swimming pools, baths and aquaria, waterworks, wells, reservoirs, by fire-fighting agencies, on maritime and naval vessels, in boilers, steam generators and locomotives, in pulp and paper mills, for irrigation and drainage, for sewage and waste disposal, in the textile industry, in the chemical industries, in the tanning industry, et cetera, and which will render said water supplies bactericidal, fungicidal and algicidal. They further provide a simple process whereby water supplies, for whatever purposes intended, are rendered bacteriostatic, fungistatic and algistatic, i.e., said water supplies treated by the process of this invention will resist and inhibit the further growth or proliferation of bacteria, fungi, algae and all forms of microbial life therein.

(II) Water Flooding in Secondary Recovery of Oil

This phase of the present invention relates to secondary recovery of oil by water flooding operations and is more particularly concerned with an improved process for treating flood water and oil recovery therewith. More particularly this invention relates to a process of inhibiting bacterial growth in the recovery of oil from oil-bearing strata by means of water flooding taking place in the presence of sulfate-reducing bacteria.

Water flooding is widely used in the petroleum industry to effect secondary recovery of oil. By employing this process the yield of oil from a given field may be increased beyond the 20-30 percent of the oil in a producing formation that is usually recovered in the primary process. In flooding operation, water is forced under pressure through injection wells into or under oil-bearing formations to displace the oil therefrom to adjacent producing wells. The oil-water mixture is usually pumped from the producing wells into a receiving tank where the water, separated from the oil, is siphoned off, and the oil then transferred to storage tanks. It is desirable in carrying out this process to maintain a high rate of water injection with a minimum expenditure of energy. Any impediment to the free entry of water into oil-bearing formations seriously reduces the efficiency of the recovery operation.

The term "flood water" as herein employed is any water injected into oil-bearing formations for the secondary recovery of oil. In conventional operations, the water employed varies from relatively pure spring water to brine and is inclusive of water reclaimed from secondary recovery operations and processed for recycling. The problems arising from the water employed depend in part on the water used. However, particularly troublesome and common to all types of water are problems directly or indirectly concerned with the presence of microorganisms, such as bacteria, fungi and algae. Microorganisms may impede the free entry of water into oil-bearing formations by producing ions susceptible of forming precipitates, forming slime and/or existing in sufficiently high numbers to constitute an appreciable mass, thereby plugging the pores of the oil-bearing formation. Free-plugging increases the pressure necessary to drive a given volume of water into an oil-bearing formation and oftentimes causes the flooding water to by-pass the formation to be flooded. In addition, microorganisms may bring about corrosion by acting on the metal structures of the wells involved, producing corrosive substances such as hydrogen sulfide, or producing conditions favorable to destructive corrosion such as decreasing the pH or producing oxygen. The products formed as the result of corrosive action may also be pore-plugging precipitates. Usually, the difficulties encountered are a combination of effects resulting from the activity of different microorganisms.

(III) Hydrocarbon Treatment

This phase of the present invention relates to the use of these compounds as biocides in hydrocarbon systems.

In addition to being used as biocides in aqueous systems, the compounds of this invention can also be employed as biocides in hydrocarbon systems, particularly when petroleum products are stored. It is believed that bacteria and other organisms, which are introduced into hydrocarbon systems by water, feed readily on hydrocarbons resulting in a loss in product; that microorganisms cause the formation of gums, $H_2S$, peroxides, acids and slimes at the interface between water and oil; that bacterial action is often more pronounced with rolling motion than under static conditions, etc. Loss of product, corrosion of the storage tank, clogging of filters and metering instruments, and fuel deterioration are among the harmful effects of bacteria growth in fuels. The activity of microorganism growth is often increased by the presence of rust. Not only do these microorganisms often encourage rust but rust encourages microorganism growth. Since microorganism growth appears to be considerably higher with kerosene than with gasoline, plugged filters experienced with jet fuels which contain large amounts of kerosene is a serious problem.

The compositions of this invention can be employed in hydrocarbon systems.

Microbiocidal Testing

The screening procedure was as follows: a one percent by weight solution of the test compound in water was prepared. The solution was aseptically added to a sterile broth that would support the growth of the test organism, Desulfovibro desulfuricans, to provide a concentration of 25, 50, 75 and 100 parts by weight of test compound per million parts by weight of broth. A general growth medium, such as prescribed by the American Petroleum Institute was used. The broth containing the test compound then was dispersed in 5 cc. amounts into sterile disposable tubes and the tubes were inoculated with the growing test organism and incubated at 35° C. for 24 hours. The absence or presence of growth of the microorganisms was determined by visual inspection by an experienced observer.

Following is a summary of the results of the testing of examples of this invention.

| Compound Example | Concentration of Test Compound |
| --- | --- |
| 2 | 50 |
| 3 | 100 |
| 5 | 75 |
| 9 | 25 |
| 10 | 50 |
| 13 | 25 |

In all of the above tests no growth of the test organism occurred, thus indicating that the compound is a biostatic or a biocide.

I claim:

1. A process inhibiting corrosion which comprises treating a system with a composition characterized by the formula

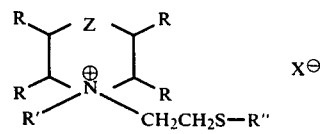

where R is hydrogen, or a hydrocarbon group, R' is a hydrocarbon group, R" is a hydrocarbon group, Z is S, SO, or $SO_2$ and X is an anion.

2. The process of claim 1 wherein R' is an alkyl group having about 4 to 18 carbons, a cyclohexyl group or a phenalkyl group, and R" is an alkyl group having about 1-8 carbons, a cycloalkyl group, an alkynyl group, or an alkenyl group.

3. The process of claim 2 where the composition has the formula

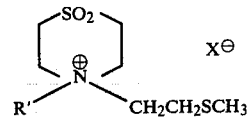

where R' is an alkyl group having 8-18 carbons.

4. The process of claim 3 where the composition has the formula

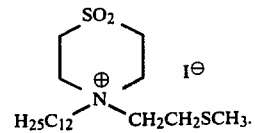

5. The process of claim 3 where the composition has the formula

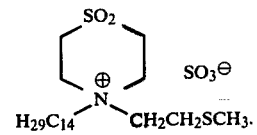

* * * * *